United States Patent
Herrmann et al.

(10) Patent No.: US 9,758,749 B2
(45) Date of Patent: Sep. 12, 2017

(54) THIOETHER DERIVATIVES AS PRECURSORS FOR A CONTROLLED RELEASE OF ACTIVE MOLECULES

(71) Applicant: Firmenich SA, Geneva (CH)

(72) Inventors: Andreas Herrmann, Geneva (CH); Peter Fankhauser, Meyrin (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 14/917,766

(22) PCT Filed: Sep. 5, 2014

(86) PCT No.: PCT/EP2014/068908
§ 371 (c)(1),
(2) Date: Mar. 9, 2016

(87) PCT Pub. No.: WO2015/032885
PCT Pub. Date: Mar. 12, 2015

(65) Prior Publication Data
US 2016/0222327 A1    Aug. 4, 2016

(30) Foreign Application Priority Data

Sep. 9, 2013  (EP) .................................. 13183486

(51) Int. Cl.
| | | |
|---|---|---|
| *C11D 3/50* | (2006.01) | |
| *C11B 9/00* | (2006.01) | |
| *C07C 323/22* | (2006.01) | |
| *C11D 3/00* | (2006.01) | |

(52) U.S. Cl.
CPC .............. *C11D 3/50* (2013.01); *C07C 323/22* (2013.01); *C11B 9/0003* (2013.01); *C11B 9/0011* (2013.01); *C11B 9/0015* (2013.01); *C11B 9/0034* (2013.01); *C11B 9/0053* (2013.01); *C11B 9/0057* (2013.01); *C11B 9/0061* (2013.01); *C11B 9/0096* (2013.01); *C11D 3/001* (2013.01); *C11D 3/507* (2013.01); *C07C 2101/14* (2013.01); *C07C 2101/16* (2013.01)

(58) Field of Classification Search
CPC ...... C07C 323/22; C11B 9/0011; C11D 3/507
See application file for complete search history.

(56) References Cited

U.S. PATENT DOCUMENTS

| | | |
|---|---|---|
| 4,137,180 A | 1/1979 | Naik et al. |
| 5,236,615 A | 8/1993 | Trinh et al. |

FOREIGN PATENT DOCUMENTS

| | | |
|---|---|---|
| EP | 0 799 885 A1 | 10/1997 |
| WO | WO8403508 A1 | 9/1984 |
| WO | WO9734986 A1 | 9/1997 |
| WO | WO03049666 A2 | 6/2003 |
| WO | WO2008044178 A1 | 4/2008 |

OTHER PUBLICATIONS

International Search Report and Written Opinion, application PCT/EP2014/068908 mailed Nov. 12, 2014.
Comasseto et al., Journ. of Organometallic Chem., 693 (2008) 2929-2936.
Ullmann's Encyclopedia of Industrial Chemistry, A8, pp. 315-448 (1987).
Ullmann's Encyclopedia of Industrial Chemistry, A25, pp. 747-817 (1994).

*Primary Examiner* — John Hardee
(74) *Attorney, Agent, or Firm* — Winston & Strawn LLP

(57) ABSTRACT

The present invention relates to the field of perfumery. More particularly, it concerns short chain β-sulfur carbonyl moieties capable of liberating an active molecule, such as a perfuming α,β-unsaturated ketone or aldehyde. The present invention concerns also the use of said compounds in perfumery as well as the perfuming compositions or perfumed articles comprising the invention's compounds.

18 Claims, No Drawings

THIOETHER DERIVATIVES AS PRECURSORS FOR A CONTROLLED RELEASE OF ACTIVE MOLECULES

This application is a 371 filing of International Patent Application PCT/EP2014/068908 filed 5 Sep. 2014, which claims the benefit of European patent application no 13183486.3 filed 9 Sep. 2013.

TECHNICAL FIELD

The present invention relates to the field of perfumery. More particularly, it concerns short chain β-sulfur carbonyl moieties capable of liberating an active molecule, namely an enone or an enal, in a very efficient way. The present invention concerns also the use of said compounds in perfumery as well as the perfuming compositions or perfumed articles comprising the invention's compounds.

PRIOR ART

The perfume industry has a particular interest for compounds which are capable of prolonging the effect of active ingredients over a certain period of time, for example in order to overcome the problems encountered when using perfuming ingredients which are too volatile or have a poor substantivity. These compounds can be used in various applications, as for example in fine or functional perfumery. The washing of textiles is a particular field in which there is a constant quest to enable the effect of active substances, in particular perfumes, to be effective for a certain period of time after washing and drying. Indeed, many substances having fragrances which are particularly suitable for this type of application are, in fact, known to lack tenacity on laundry, or do not remain on the laundry when rinsed, with the result that their perfuming effect is experienced only briefly and not very intensely. Given the importance of this type of application in the perfume industry, research in this field has been sustained, in particular with the aim of finding new and more effective solutions to the aforementioned problems.

WO 03/049666 discloses compounds similar to the present ones but differing by having a longer/heavier tail (the present S—R moiety). It is clearly mentioned in the prior art that it is desirable to achieve a positive olfactive effect and in that perspective the resulting thiol RSH should be odorless and it is recommended to use at least $C_8$ thiol or heavier ones, such as the $C_{12}$ or $C_{18}$ exemplified therein. In fact, said prior art document establishes a real negative a priori against using short chain thiols, which is the subject of the present invention.

Moreover, with a compound of the present invention another prejudice in the art against their use is that a skilled person could expect that deposition and the olfactive performance of a pro-fragrance would be negatively impacted by the use of short chain being more hydrophilic.

However, the prior art pro-fragrances present the problem of not being very atom-efficient, in the sense that the weight ratio perfume/pro-fragrance is quite low.

The aim of the present invention is to provide new pro-fragrances being more atom-efficient while delivering as good as, or superior, olfactive performances.

DESCRIPTION OF THE INVENTION

We have, surprisingly, discovered that short chain β-sulfur carbonyl moieties are capable of liberating an active molecule, namely an enone or an enal, in a very efficient way and with improved long-lasting olfactive performance, despite all the prejudice in the art against the use of such compounds. As "active molecule" we mean here any molecule capable of bringing an odor benefit or effect into its surrounding environment, and in particular an odoriferous molecule, i.e. a perfuming ingredient, such as an α,β-unsaturated ketone or aldehyde.

The compound of the present invention (a thioether derivative) is of formula

wherein P represents a group susceptible of generating a perfuming α,β-unsaturated ketone or aldehyde and is represented by formula

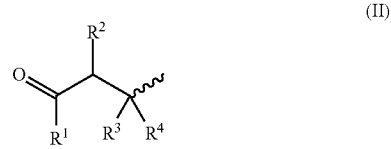

in which the wavy line indicates the location of the bond between said P and the sulfur atom;

$R^1$ represents a hydrogen atom, a $C_1$ to $C_{15}$ linear, cyclic or branched alkyl, alkenyl or alkadienyl radical, possibly substituted by $C_1$ to $C_4$ alkyl groups; and $R^2$, $R^3$ and $R^4$ represent a hydrogen atom, an aromatic ring or a $C_1$ to $C_{15}$ linear, cyclic or branched alkyl, alkenyl or alkadienyl radical, possibly substituted by $C_1$ to $C_4$ alkyl groups; or two, or three, of the groups $R^1$ to $R^4$ are bonded together to form a saturated or unsaturated ring having 6 to 20 carbon atoms and including the carbon atom to which said $R^1$, $R^2$, $R^3$ or $R^4$ groups are bonded, this ring being possibly substituted by $C_1$ to $C_8$ linear, branched or cyclic alkyl or alkenyl groups;

X represents a functional group selected from the group consisting of the formulae i) to iii)

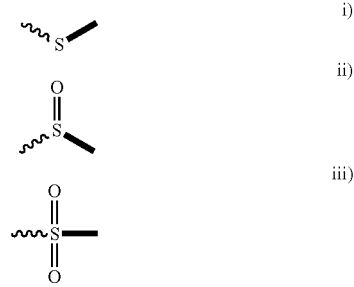

in which formulae the wavy lines are as defined previously and the bold lines indicate the location of the bond between said X and R; and R represents a $C_{3-5}$ alkyl, cycloalkyl or alkenyl group optionally comprising from 1 or 2 functional groups selected amongst $NO_2$, ether, alcohol and thioether.

As "a perfuming α,β-unsaturated ketone or aldehyde", expression used in the definition of P, we mean here an α,β-unsaturated ketone or aldehyde which is recognized by a person skilled in the art as being used in perfumery as perfuming ingredient. By "perfuming ingredient" it is meant here a compound, which is used in a perfuming preparation or a composition to impart a hedonic effect. In other words such perfuming ingredient, to be considered as being a perfuming one, must be recognized by a person skilled in the art as being able to impart or modify in a positive or pleasant way the odor of a composition, and not just as having an odor.

In general, said odoriferous α,β-unsaturated ketone or aldehyde is a compound having from 8 to 20 carbon atoms, or even more, preferably between 10 and 15 carbon atoms.

According to any embodiment of the invention, P may represent a group of the formulae (P-1) to (P-12), in the form of any one of its isomers:

(P-1)
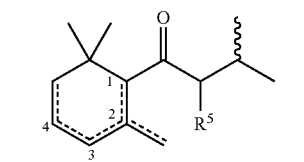

(P-2)
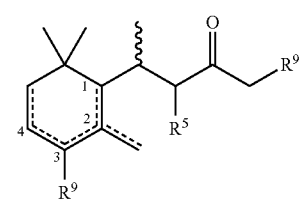

(P-3)
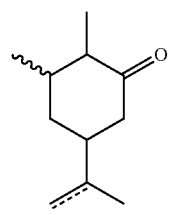

(P-4)
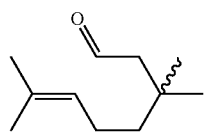

(P-5)
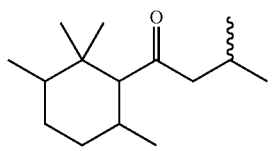

(P-6)
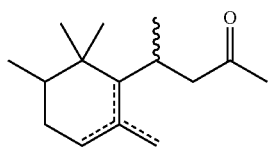

(P-7)
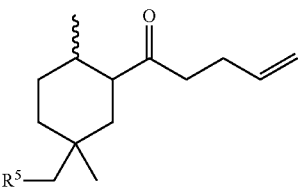

(P-8)
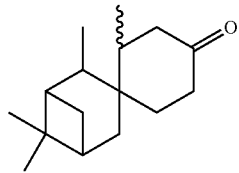

(P-9)
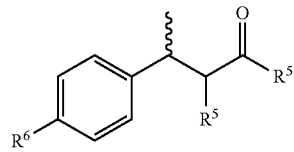

(P-10)
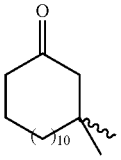

(P-11)
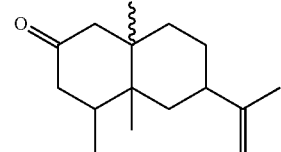

(P-12)
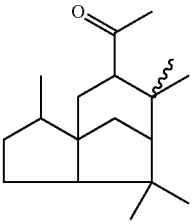

in which formulae the wavy lines have the meaning indicated above and the dotted lines represent a single or double bond, $R^5$ being a hydrogen atom or a methyl group and $R^6$ representing a hydrogen atom, a hydroxy or methoxy group or a $C_1$-$C_4$ linear or branched alkyl group.

According to any embodiment of the invention, P may represent a group of the formula (P-1)'
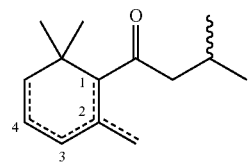

(P-2)'
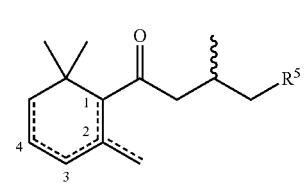

(P-3)

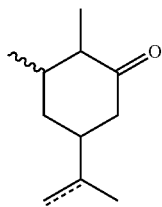

(P-4)

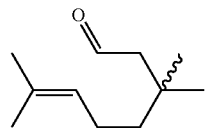

(P-5)

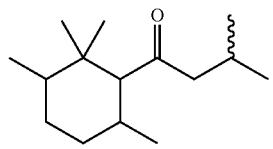

(P-6)

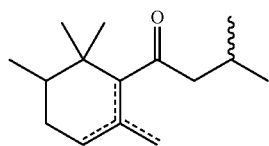

(P-7)

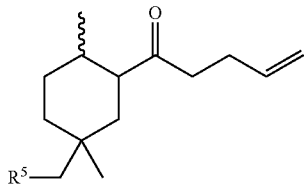

(P-9)

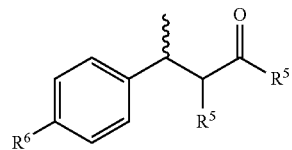

wherein the wavy lines, $R^5$ and $R^6$ have the meaning indicated above.

According to any embodiment of the invention, P may represent a radical of the formula (P-1'), (P-2), (P-3), (P-4) or (P-7) as defined above. Even more particularly P may represent a compound of formula (P-1), (P-3), or (P-4).

According to any one of the invention's embodiments, said group P is a group susceptible of generating an odoriferous compound selected amongst: alpha-damascone, beta-damascone, gamma-damascone, delta-damascone, alpha-ionone, beta-ionone, gamma-ionone, delta-ionone, beta-damascenone, 1-(5,5- or 3,3-dimethyl-1-cyclohexen-1-yl)-4-penten-1-one, 2-methyl-5-(prop-1-en-2-yl)cyclohex-2-enone (carvone), 8- or 10-methyl-alpha-ionone, 1-(2,2,3,6-tetramethyl-1-cyclohexyl)-2-buten-1-one, 4-(2,2,3,6-tetramethyl-1-cyclohexyl)-3-buten-2-one, nootkatone, cinnamic aldehyde, 2,6,6-trimethyl-bicyclo[3.1.1]heptane-3-spiro-1-cyclohexen-4'-one and 3,7-dimethylocta-2,6-dienal (citral).

Amongst the odoriferous compounds cited in the list hereinabove, it will be preferably selected: the damascones, ionones, beta-damascenone, 1-(5,5- or 3,3-dimethyl-1-cyclohexen-1-yl)-4-penten-1-one, carvone, 1-(2,2,3,6-tetramethyl-1-cyclohexyl)-2-buten-1-one, 4-(2,2,3,6-tetramethyl-1-cyclohexyl)-3-buten-2-one and citral.

According to any embodiment of the invention, X represents a functional group of formula i) (i.e. a thioether), as previously defined.

For the sake of clarity, by the expression "alkenyl" it is here meant a group which comprises one carbon-carbon double bond in any position of the chain provided that said double bond is not conjugated with the sulfur atom.

According to any embodiment of the invention, R represents a $C_{3-5}$ alkyl or cycloalkyl group optionally comprising one functional group selected amongst the ether and thio-ether groups.

According to any embodiment of the invention, R represents a branched or cyclic alkyl group, in particular wherein one of formula $CHR^aR^b$ wherein $R^a$ and $R^b$ can be taken separately (a branched group) or together (a cyclic group).

According to any embodiment of the invention, R represents a $C_{3, 4 \text{ or } 5}$ linear or branched or cyclic alkyl group. In particular one may cite as R group an iso-propyl, n-butyl, n-pentyl group.

The compounds of formula (I) may be synthesized from commercially available compounds by conventional methods. Generally speaking, the invention's compounds are obtainable by the [1,4]-addition reaction between an odoriferous α,β-unsaturated ketone or aldehyde of formula

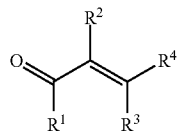

(III)

wherein the configuration of the carbon-carbon double bond can be of the E or Z type and the symbols $R^1$, $R^2$, $R^3$ and $R^4$ have the meaning indicated above; and a compound of formula R—SH, wherein all the symbols have the meaning given in formula (I). Then optionally the sulfur atom can be oxidized according to standard methods into a functional group of formula ii) or iii).

Specific examples or alternative approaches are described in the examples herein below.

It is understood that the α,β-unsaturated ketones or aldehydes of formulae (III) are the odoriferous compounds released by the compound of formula (I) upon decomposition. It has to be pointed out that the release of the α,β-unsaturated ketones or aldehydes produces also a residue derived from the moiety R—S—, and which according to the prior art teaching (WO 03/049666) is a thiol of formula RSH, i.e. in the present case very short chain thiols which are known to have very strong and very unpleasant odors which would be highly detrimental to the olfactive effect delivered by the present compound upon use.

We have here very surprisingly found that, as shown in the examples, despite that one could have expected very unpleasant odor, the present compound is in fact a valuable perfuming ingredient capable of delivering a positive hedonic effect upon decomposition.

As mentioned above, the invention concerns the use of a compound of formula (I) as perfuming ingredient. In other words, it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing a compound (I) and which can be advantageously employed in perfumery industry.

Said compositions, which in fact can be advantageously employed as perfuming ingredients, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also water (in which case a solubilizing amount of surfactants may be necessary), ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carriers one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs-und Geliermittel in Lebensmitteln, Band 2 der Schriftenreihe Lebensmittelchemie, Lebensmittelqualität, Behr's Verlag GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation technique.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulfurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds, or can be an encapsulated perfume.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

A particular aspect of the invention perfumery compositions concerns the ones further comprising (in addition to the above composition):
at least one compound selected amongst the isothiazolones of formula

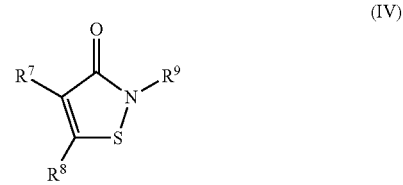

(IV)

wherein $R^7$ and $R^8$ represent, separately and independently of each other, a hydrogen atom, a halogen atom, preferably chlorine, a $C_1$-$C_4$ linear or branched alkyl group, an amino group or a benzylamino group; or, alternatively, $R^7$ and $R^8$ are taken together to represent a phenyl or pyridine ring, possibly substituted with one to four $C_1$-$C_4$ linear or branched alkyl or alkenyl groups and/or one to two halogen atoms, preferably chlorine atoms; and
$R^9$ represents a hydrogen atom, an alkali metal atom, in particular Na or K, a phenyl or benzyl group possibly substituted with one or two halogen atoms and/or one or two methyl, trifluoromethyl, methoxy or amino groups, an amine group, or a $C_1$-$C_8$ unsaturated, linear, branched or cyclic hydrocarbon group possibly substituted with one or two nitrogen, oxygen or halogen atoms.

According to a particular embodiment of the invention said compound of formula (IV) is one wherein $R^7$ and $R^8$ represent, separately and independently of each other, a hydrogen atom, a chlorine atom or a methyl group or, alternatively, $R^7$ and $R^8$ are taken together to represent a phenyl ring, and $R^9$ represents a hydrogen atom or a methyl group.

According to a particular embodiment of the invention, said compound of formula (IV) is selected from the group of isothiazolones consisting of 1,2-benzisothiazol-3(2H)-one, 4- or 5-chloro-2-methylisothiazol-3(2H)-one or 2-methylisothiazol-3(2H)-one, or more preferably 5-chloro-2-methylisothiazol-3(2H)-one or 1,2-benzisothiazol-3(2H)-one, and most preferably 1,2-benzisothiazol-3(2H)-one.

According to a particular embodiment of the invention, said compound (IV) is present in the compositions of the invention at a weight concentration of 0.0% to 5%, relative to the total weight of the composition. According to more preferred embodiments of the invention, the concentration of compound of formula (IV) is comprised between 0.001 and 3% of the total weight, preferably between 0.005 and 0.1%.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

Furthermore, the invention's compound can also be advantageously used in all the fields of modern perfumery, i.e. fine or functional perfumery, to positively impart or modify the odor of a consumer product into which said compound (I) is added. Indeed, for example, the invention's compounds are capable of levitating problems often encountered with classical perfuming ingredients present as such which in washing or perfuming compositions can have little staying-power on a surface and consequently are often eliminated, for example in the rinsing water or upon drying of surfaces such as textiles, hard surfaces, hair and skin.

Consequently, a perfuming consumer product which comprises:
i) as perfuming ingredient, at least one compound of formula
   (I) or a perfuming composition, as defined above; and
ii) a perfumery consumer base;
is also an object of the present invention.

The invention's compound can be added as such or as part of an invention's perfuming composition.

For the sake of clarity, it has to be mentioned that, by "perfuming consumer product" it is meant a consumer product which is expected to deliver at least a perfuming effect, in other words it is a perfumed consumer product. For the sake of clarity, it has to be mentioned that, by "perfumery consumer base" we mean here the functional formulation, as well as optionally additional benefit agents, corresponding to a consumer product which is compatible with perfuming ingredients and is expected to deliver a pleasant odor to the surface to which it is applied (e.g. skin, hair, textile, or home surface). In other words, a perfuming consumer product according to the invention comprises the functional formulation, as well as optionally additional benefit agents, corresponding to the desired consumer product, e.g. a detergent or an air freshener, and an olfactive effective amount of at least one invention's compound.

The nature and type of the constituents of the perfumery consumer base do not warrant a more detailed description here, which in any case would not be exhaustive, the skilled person being able to select them on the basis of his general knowledge and according to the nature and the desired effect of said product.

Non-limiting examples of suitable perfumery consumer base can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Preferred perfuming compositions or perfumed articles are perfumes, fabric or hard-surface detergents and fabric softeners or refreshers.

Typical examples of fabric detergents or softener compositions into which the compounds of the invention can be incorporated are described in WO 97/34986, or in U.S. Pat. Nos. 4,137,180 and 5,236,615 or in EP 799 885. Other typical detergents and softening compositions which can be used are described in works such as Ullman's Encyclopedia of Industrial Chemistry, vol. A8, pages 315-448 (1987) and vol. A25, pages 747-817 (1994); Flick, Advanced Cleaning Product Formulations, Noye Publication, Park Ridge, N.J. (1989); Showell, in Surfactant Science Series, vol. 71: Powdered Detergents, Marcel Dekker, New York (1988); Proceedings of the World Conference on Detergents (4th, 1998, Montreux, Switzerland), AOCS print.

Some of the above-mentioned consumer product bases may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat, oxidation or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.001% to 5% by weight, or even more, of the compounds of the invention based on the weight of the composition into which they are incorporated. Concentrations lower than these, such as in the order of 0.01% to 1 or 2% by weight, can be used when these compounds are incorporated into perfumed articles, percentage being relative to the weight of the article.

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 400 or 500 MHz machine for $^1H$ and with 100 or 125 MHz for $^{13}C$, the chemical displacement δ are indicated in ppm with respect to the TMS as standard, the coupling constants J are expressed in Hz.

Example 1

Synthesis of Compounds of Formula (I)

a) 3-(butylthio)-1-((1S,2R)-2,6,6-trimethylcyclohex-3-en-1-yl)butan-1-one (I-C4)

1,8-Diazabicyclo-5,4,0-undecene (DBU, 0.4 g, 2.6 mmol) was added to a mixture of (E)-1-((1S,2R)-2,6,6-trimethylcyclohex-3-enyl)but-2-en-1-one (delta-damascone, 14.9 g, 78.0 mmol) and 1-butanethiol (7.0 g, 78.0 mmol). After 30 minutes the reaction was quenched with 20% aqueous citric acid. The reaction mixture was diluted with methyl tert-butylmethylether (50 ml), washed with $H_2O$ (2×20 ml) and brine (20 ml), dried over anhydrous $Na_2SO_4$, filtered and concentrated in vacuo. The residue (26.0 g) was purified by flash distillation (Kugelrohr, 115-120° C., 0.1 mbar) to yield the pure compound as a yellow oil (18.5 g, 65.5 mmol, 84%, mixture of 2 diastereomers).

$^{13}$C-NMR: 13.7 (q), 19.9 (q), 20.7 (q), 21.6/21.8 (q), 22.1 (t), 29.8 (q), 30.5/30.6 (t), 31.6/31.8 (d), 31.8 (t), 33.0/33.2 (s), 34.1 (d), 41.7 (t), 55.2/55.3 (t), 62.8/63.0 (d), 124.1/124.2 (d), 131.8 (d), 212.4/212.5 (s);

$^{1}$H-NMR: 0.87-1.00 (m, 12H); 1.26-1.32 (m, 3H); 1.36-1.45 (m, 2H); 1.53-1.61 (m, 2H); 1.65-1.74 (m, 1H); 1.92-2.01 (m, 1H); 2.18-2.24 (m, 1H); 2.47-2.57 (m, 3.5H); 2.69-2.73 (m, 1H); 2.87-2.95 (m, 0.5H); 3.25-3.36 (m, 1H); 5.42-5.48 (m, 1H); 5.50-5.57 (m, 1H).

b) 3-(pentylthio)-1-((1S,2R)-2,6,6-trimethylcyclohex-3-en-1-yl)butan-1-one (I-C5)

This compound was synthesized from delta-damascone and 1-pentanethiol as described above.

$^{13}$C-NMR: 14.0 (q), 19.9 (q), 20.7 (q), 21.6/21.8 (q), 22.3 (t), 29.4 (t), 29.8 (q), 30.8/30.9 (t), 31.2 (t), 31.6/31.8 (d), 33.1/33.2 (s), 34.1 (d), 41.8 (t), 55.2/55.4 (t), 62.8/62.9 (d), 124.1/124.3 (d), 131.8 (d), 212.3/212.4 (s);

$^{1}$H-NMR: 0.87-0.93 (m, 6H); 0.93-1.01 (m, 6H); 1.26-1.41 (m, 7H); 1.54-1.64 (m, 2H); 1.65-1.74 (m, 1H); 1.92-2.01 (m, 1H); 2.18-2.24 (m, 1H); 2.47-2.58 (m, 3.5H); 2.69-2.73 (m, 1H); 2.87-2.95 (m, 0.5H); 3.25-3.36 (m, 1H); 5.42-5.48 (m, 1H); 5.50-5.57 (m, 1H).

c) 3-(hexylthio)-1-((1S,2R)-2,6,6-trimethylcyclohex-3-en-1-yl)butan-1-one (I-C6)

This compound was synthesized from delta-damascone and 1-hexanethiol as described above.

$^{13}$C-NMR: 14.0 (q), 19.9 (q), 20.7 (q), 21.6/21.8 (q), 22.5 (t), 28.7 (t), 29.7 (t), 29.8 (q), 30.9 (t), 31.4 (t), 31.6/31.8 (d), 33.2/33.0 (s), 34.1 (d), 41.8 (t), 55.2/55.4 (t), 62.8/63.0 (d), 124.1/124.3 (d), 131.8 (d), 212.4/212.5 (s);

$^{1}$H-NMR: 0.85-0.93 (m, 6H); 0.93-1.01 (m, 6H); 1.25-1.33 (m, 7H); 1.33-.1.43 (m, 2H); 1.53-1.63 (m, 2H); 1.65-1.74 (m, 1H); 1.92-2.01 (m, 1H); 2.18-2.24 (m, 1H); 2.47-2.57 (m, 3.5H); 2.69-2.73 (m, 1H); 2.87-2.95 (m, 0.5H); 3.25-3.36 (m, 1H); 5.42-5.48 (m, 1H); 5.50-5.57 (m, 1H).

d) 3-(butylthio)-3,7-dimethyloct-6-enal (II-C4)

This compound was prepared from (E)-3,7-dimethylocta-2,6-dienal (citral; 8.44 g, 55.4 mmol), DBU (0.5 g) and 1-butanethiol (5.0 g, 55.4 mmol) according to the procedure described above. The resulting crude material (12.5 g), containing some residual citral can be used as such. Further purification by vacuum distillation (bulb to bulb, 90-95° C., 0.1 mbar) afforded 7.5 g (55% yield) of pure title compound (99%).

$^{13}$C-NMR: 13.7 (q), 17.6 (q), 22.3 (t), 22.8 (t), 25.7 (q), 26.3 (q), 27.1 (t), 31.3 (t), 41.0 (t), 45.7 (s), 52.6 (t), 123.5 (d), 132.2 (s), 201.7 (d);

$^{1}$H-NMR: 0.91 (t, J=7.2 Hz, 3H); 1.38-1.45 (m, 2H); 1.41 (s, 3H); 1.51-1.57 (m, 2H); 1.60-1.64 (m, 2H); 1.62 (s, 3H); 1.68 (s, 3H); 2.04-2.18 (m, 2H); 2.49 (t, J=7.2 Hz, 2H); 2.52-2.58 (m, 2H); 5.06-5.11 (m, 1H); 9.86 (t, J=2.9 Hz, 1H).

e) 3-(pentylthio)-3,7-dimethyloct-6-enal (II-C5)

This compound was synthesized from citral and 1-pentanethiol as described above.

$^{13}$C-NMR: 13.9 (q), 17.6 (q), 22.3 (t), 22.8 (t), 25.7 (q), 26.3 (q), 27.4 (t), 28.9 (t), 31.4 (t), 41.0 (t), 45.7 (s), 52.6 (t), 123.5 (d), 132.2 (s), 201.7 (d);

$^{1}$H-NMR: 0.89 (t, J=7.3 Hz, 3H); 1.28-1.39 (m, 4H); 1.41 (s, 3H); 1.51-1.58 (m, 2H); 1.59-1.64 (m, 2H); 1.62 (s, 3H); 1.68 (s, 3H); 2.04-2.18 (m, 2H); 2.48 (t, J=7.4 Hz, 2H); 2.48-2.57 (m, 2H); 5.06-5.11 (m, 1H); 9.86 (t, J=2.9 Hz, 1H).

f) 3-(hexylthio)-3,7-dimethyloct-6-enal (II-C6)

This compound was synthesized from citral and 1-hexanethiol as described above.

$^{13}$C-NMR: 14.0 (q), 17.6 (q), 22.5 (t), 22.8 (t), 25.7 (q), 26.3 (q), 27.5 (t), 28.9 (t), 29.2 (t); 31.4 (t), 41.0 (t), 45.7 (s), 52.6 (t), 123.5 (d), 132.2 (s), 201.7 (d);

$^{1}$H-NMR: 0.89 (t, J=7.3 Hz, 3H); 1.25-1.32 (m, 4H); 1.36-1.40 (m, 2H); 1.40 (s, 3H); 1.52-1.57 (m, 2H); 1.59-1.64 (m, 2H); 1.62 (s, 3H); 1.69 (s, 3H); 2.04-2.18 (m, 2H); 2.48 (t, J=7.4 Hz, 2H); 2.48-2.57 (m, 2H); 5.06-5.11 (m, 1H); 9.86 (t, J=2.9 Hz, 1H).

g) 3-(butylthio)-2-methyl-5-(prop-1-en-2-yl)cyclohexanone (III-C4)

This compound was synthesized from (R)-2-methyl-5-(prop-1-en-2-yl)cyclohex-2-enone (carvone gauche; 8.33 g, 55.4 mmol), DBU (0.5 g) and 1-butanethiol (5.0 g, 55.4 mmol) as described above. The resulting crude material (12.0 g), containing some residual carvone gauche can be used as such. Further purification by vacuum distillation (bulb to bulb, 90-95° C., 0.1 mbar) afforded 7.0 g (53% yield) of pure title compound (95%).

$^{13}$C-NMR: 12.6 (q), 13.6 (q), 20.8 (q), 22.0 (t), 31.7 (t), 31.8 (t), 35.9 (t), 40.7 (d), 46.0 (t), 48.8 (d), 49.6 (d), 110.1 (t), 147.2 (s), 209.9 (s);

$^{1}$H-NMR: 0.91 (t, J=7.4 Hz, 3H); 1.16 (d, J=6.8 Hz, 3H); 1.36-1.44 (m, 2H); 1.52-1.58 (m, 2H); 1.76 (s, 3H); 1.96-2.02 (m, 1H); 2.15-2.20 (m, 1H); 2.21-2.27 (m, 1H); 2.45-2.54 (m, 3H); 2.77-2.83 (m, 1H); 2.90-2.97 (m, 1H); 3.38-3.42 (m, 1H); 4.77 (br, 1H); 4.81 (br, 1H).

h) 3-(pentylthio)-2-methyl-5-(prop-1-en-2-yl)cyclohexanone (III-C5)

This compound was synthesized from carvone gauche and 1-pentanethiol as described above.

$^{13}$C-NMR: 12.6 (q), 14.0 (q), 20.8 (q), 22.3 (t), 29.3 (t), 31.0 (t), 32.1 (t), 35.9 (t), 40.7 (d), 46.0 (t), 48.8 (d), 49.7 (d), 110.1 (t), 147.2 (s), 209.9 (s);

$^{1}$H-NMR: 0.89 (t, J=7. Hz, 3H); 1.16 (d, J=6.8 Hz, 3H); 1.27-1.39 (m, 4H); 1.52-1.59 (m, 2H); 1.76 (s, 3H); 1.96-2.02 (m, 1H); 2.15-2.20 (m, 1H); 2.20-2.26 (m, 1H); 2.45-2.53 (m, 3H); 2.77-2.83 (m, 1H); 2.90-2.978 (m, 1H); 3.38-3.42 (m, 1H); 4.77 (br, 1H); 4.81 (br, 1H).

i) 3-(hexylthio)-2-methyl-5-(prop-1-en-2-yl)cyclohexanone (III-C6)

This compound was synthesized from carvone gauche and 1-hexanethiol as described above.

$^{13}$C-NMR: 12.6 (q), 14.0 (q), 20.8 (q), 22.5 (t), 28.6 (t), 29.6 (t), 31.4 (t), 32.2 (t), 35.9 (t), 40.7 (d), 46.0 (d), 48.8 (d), 49.7 (d), 110.1 (t), 147.2 (s), 209.9 (s);

$^{1}$H-NMR: 0.89 (t, J=7.0 Hz, 3H); 1.16 (d, J=6.8 Hz, 3H); 1.23-1.33 (m, 4H); 1.33-1.41 (m, 2H); 1.52-1.59 (m, 2H); 1.76 (s, 3H); 1.96-2.02 (m, 1H); 2.15-2.20 (m, 1H); 2.20-2.26 (m, 1H); 2.44-2.54 (m, 3H); 2.77-2.83 (m, 1H); 2.90-2.978 (m, 1H); 3.38-3.42 (m, 1H); 4.77 (br, 1H); 4.81 (br, 1H).

j) 3-(Isopropylthio)-1-((1S,2R)-2,6,6-trimethylcyclohex-3-en-1-yl)butan-1-one (I-isoC3)

This compound was synthesized from delta-damascone and 2-propanethiol as described above.

$^{13}$C-NMR: 19.9/19.9 (q), 20.7 (q), 22.0/2 (q), 23.5 (q), 23.6 (q), 29.8 (q), 31.6/31.8 (d), 32.9 (d), 33.0 (s), 34.1/34.2 (d), 41.7 (t), 55.5/55.6 (t), 62.8/62.9 (d), 124.1/124.2 (d), 131.8/131.9 (d), 212.4/212.5 (s);

$^{1}$H-NMR: 0.88-0.92 (m, 3H); 0.94-1.0 (m, 6H); 1.24-1.31 (m, 9H); 1.66-1.73 (m, 1H); 1.93-2.00 (m, 1H); 2.18-2.24 (m, 1H); 2.48-2.57 (m, 1.5H); 2.68-2.73 (m, 1H); 2.86-2.93 (m, 0.5H); 2.96-3.05 (m, 1H); 3.33-3.41 (m, 1H); 5.42-5.47 (m, 1H); 5.50-5.57 (m, 1H).

k) 1-(2-(Isopropylthio)-5,5-dimethylcyclohexyl)pent-4-en-1-one

This compound was prepared from 1-(5,5-dimethylcyclohex-2-en-1-yl)pent-4-en-1-one (Neobutenone® alpha, origin: Firmenich SA, 10.0 g, 52.0 mmol), DBU (0.4 g) and 2-propanethiol (3.96 g, 52.0 mmol) according to the procedure described above. The resulting crude material (14.0 g), containing some residual Neobutenone® can be used as such. Further purification by vacuum distillation (15 cm Vigreux column, 80° C., 0.1 mbar) afforded 8.2 g (59% yield) of pure title compound as a 75/25 trans/cis isomer mixture. Analysis samples of pure isomers were prepared by chromatography (SiO$_2$, heptane/MTBE 93/7).

Trans Isomer:

$^{13}$C-NMR: 23.6 (q), 24.0 (q), 24.2 (q), 27.3 (t), 30.0 (s), 31.2 (t), 32.4 (q), 35.3 (d), 39.0 (t), 42.8 (t), 42.8 (t), 43.3 (d), 52.4 (d), 115.0 (t), 137.4 (d), 212.3 (s);

$^{1}$H-NMR: 0.92 (s, 3H); 0.93 (s, 3H); 1.19 (d, J=6.6 Hz; 3H); 1.23 (d, J=6.6 Hz; 3H); 1.25-1.32 (m, 2H); 1.39-1.46 (m, 2H); 1.50-1.63 (m, 1H); 1.91-1.98 (m, 1H); 2.30-2.37 (m, 2H); 2.61 (t, J=7.5 Hz, 2H); 2.67-2.73 (m, 2H); 2.89-2.99 (m, 1H); 4.95-5.08 (m, 1H); 5.78-5.88 (m, 1H).

Cis Isomer:

$^{13}$C-NMR: 23.6 (q), 24.0 (q), 24.2 (q), 27.3 (t), 30.0 (s), 31.2 (t), 32.4 (q), 35.3 (d), 39.0 (t), 42.8 (t), 42.8 (t), 43.3 (d), 52.4 (d), 115.0 (t), 137.4 (d), 212.3 (s);

$^{1}$H-NMR: 0.88 (s, 3H); 0.98 (s, 3H); 1.16-1.26 (m, 2H); 1.21 (d, J=6.6 Hz; 3H); 1.24 (d, J=6.6 Hz; 3H); 1.40-1.47 (m, 1H); 1.56 (t, J=13.4, 1H); 1.64-1.78 (m, 2H); 1.88-1.98 (m, 1H); 2.30-2.37 (m, 2H); 2.53-2.66 (m, 2H); 2.67-2.74 (m, 1H); 2.78-2.88 (m, 1H); 4.94-5.08 (m, 2H); 5.78-5.88 (m, 1H).

l) 1-(2-(Butylthio)-5,5-dimethylcyclohexyl)pent-4-en-1-one

This compound was synthesized from Neobutenone® alpha and 1-butanethiol as described above.

Trans Isomer:

$^{13}$C-NMR: 13.7 (q), 22.0 (t), 24.2 (q), 27.3 (t), 30.0 (s), 30.3 (t), 31.1 (t), 32.0 (t), 32.4 (q), 38.9 (t), 42.6 (t), 42.8 (t), 44.4 (d), 52.2 (d), 115.0 (t), 137.4 (d), 212.3 (s);

$^{1}$H-NMR: 0.89 (t, J=7.1 Hz, 3H); 0.92 (s, 3H); 0.94 (s, 3H); 1.16-1.29 (m, 2H); 1.33-1.40 (m, 2H); 1.40-1.46 (m, 2H); 1.48-1.54 (m, 2H); 1.54-1.60 (m, 1H); 1.93-1.99 (m, 1H); 2.31-2.37 (m, 2H); 2.48-2.52 (m, 2H); 2.59-2.64 (m, 2H); 2.65-2.73 (m, 2H); 4.95-5.07 (m, 2H); 5.78-5.88 (m, 1H).

Cis Isomer:

$^{13}$C-NMR: 13.7 (q), 22.0 (t), 24.4 (q), 27.7 (t), 28.0 (t), 30.1 (t), 31.7 (t), 32.1 (t), 32.9 (q), 33.1 (t), 35.6 (t), 39.3 (t), 44.9 (d), 50.3 (d), 114.9 (t), 137.6 (d), 210.3 (s);

$^{1}$H-NMR: 0.88 (s, 3H); 0.89 (t, J=7.1 Hz, 3H); 0.98 (s, 3H); 1.16-1.621 (m, 6H); 1.66-1.72 (m, 1H); 1.76-1.81 (m, 1H); 1.86-1.91 (m, 1H); 2.31-2.37 (m, 2H); 2.42-2.48 (m, 2H); 2.53-2.74 (m, 4H); 3.38-3.41 (m, 1H); 4.95-4.99 (m, 1H); 5.02-5.07 (m, 1H); 5.79-5.88 (m, 1H).

m) 1-(2-(Pentylthio)-5,5-dimethylcyclohexyl)pent-4-en-1-one

This compound was synthesized from Neobutenone® alpha and 1-pentanethiol as described above.

Trans Isomer:

$^{13}$C-NMR: 14.0 (q), 22.3 (t), 24.2 (q), 27.3 (t), 29.6 (t), 30.0 (s), 30.3 (t), 31.1 (t), 31.4 (t), 32.4 (q), 38.9 (t), 42.6 (t), 42.8 (t), 44.4 (d), 52.2 (d), 115.0 (t), 137.4 (d), 212.2 (s);

$^{1}$H-NMR: 0.89 (t, J=7.1 Hz, 3H); 0.92 (s, 3H); 0.94 (s, 3H); 1.15-1.28 (m, 2H); 1.28-1.36 (m, 4H); 1.39-1.46 (m, 2H); 1.48-1.62 (m, 3H); 1.93-1.99 (m, 1H); 2.30-2.37 (m, 2H); 2.47-2.52 (m, 2H); 2.59-2.64 (m, 2H); 2.65-2.73 (m, 2H); 4.94-5.07 (m, 2H); 5.78-5.88 (m, 1H).

Cis Isomer:

$^{13}$C-NMR: 14.0 (q), 22.3 (t), 24.4 (q), 27.7 (t), 28.0 (t), 29.4 (t), 30.1 (s); 32.4 (t), 31.1 (t), 32.9 (q), 33.2 (t), 35.6 (t), 39.3 (t), 44.9 (d), 50.3 (d), 114.9 (t); 137.6 (d), 210.2 (s);

$^{1}$H-NMR: 0.88 (s, 3H); 0.89 (t, J=7.1 Hz, 3H); 0.98 (s, 3H); 1.16-1.621 (m, 8H); 1.65-1.73 (m, 1H); 1.76-1.82 (m, 1H); 1.86-1.91 (m, 1H); 2.31-2.37 (m, 2H); 2.41-2.47 (m, 2H); 2.53-2.74 (m, 4H); 3.38-3.41 (m, 1H); 4.95-4.99 (m, 1H); 5.02-5.07 (m, 1H); 5.79-5.88 (m, 1H).

Example 2

Performance of a Fabric Softener Base Comprising an Invention's Compound of Formula (I) and Comparison with the Prior-Art The liberation of delta-damascone, citral or carvone gauche from the present invention's compounds of formula (I) was tested in a fabric softening surfactant emulsion with the following final composition:

| | |
|---|---|
| Stepantex ® VL90 A (origin: Stepan) | 16.5% by weight |
| Calcium chloride (10% aq. solution) | 0.6% by weight |
| Water | 82.9% by weight |

The different compounds prepared in Example 1 were individually dissolved in ethanol (3 ml) at a concentration to release a total amount of 0.135 mmol of the fragrance and then dispersed in the above described fabric softening surfactant emulsion (5.40 g). The samples were shaken and left standing overnight.

In a beaker, the fabric softening surfactant emulsion containing the compound of formula (I) (2.60 g) was diluted with demineralised cold tap water (600 g) and one cotton sheet (EMPA cotton test cloth Nr. 221, origin: Eidgenössische Materialprüfanstalt (EMPA), pre-washed with an unperfumed detergent powder and cut to ca. 12×12 cm sheets) was added to each beaker. The sheet was manually stirred for 3 min, left standing for 2 min, then wrung out by hand and line-dried for 1 day. As a reference sample, the prior art compound 3-(dodecylthio)-1-(2,6,6-trimethyl-3-cyclohexen-1-yl)-1-butanone (described as Example 4a in WO 03/049666) or an equimolar amount of the corresponding unmodified free reference fragrance were prepared and treated in the same way as described above. All measurements were performed at least twice.

One dry cotton sheet was put into a headspace sampling cell (internal volume ca. 160 ml), thermostatted at 25° C. and exposed to a constant air flow (200 ml/min), respectively. The air was filtered through active charcoal and aspirated through a saturated solution of NaCl, corresponding to a constant humidity of ca. 75%. During 15 min, the volatiles were adsorbed onto a waste Tenax® cartridge, then during 15 min onto a clean Tenax® cartridge. The sampling was repeated 7 times every 60 min (45 min trapping on the waste cartridge and 15 min on a clean cartridge); the waste cartridges were discarded. The cartridges with the volatiles were thermally desorbed on a Perkin Elmer TurboMatrix ATD desorber coupled to an Agilent Technologies 7890A GC System equipped with a HP-1 capillary column (30 m, i.d. 0.32 mm, film 0.25 μm) and a flame ionization detector (FID). The volatiles were analyzed using a temperature gradient from 60° C. to 200° C. at 15° C./min Headspace concentrations (in ng/l of air) were obtained by external standard calibration with different concentrations of the delta-damascone, citral or carvone gauche to be liberated. The headspace concentrations measured after 150 min of sampling above the dry cotton sheets are listed in the Table 1 below.

TABLE 1

Average headspace concentrations of delta-damascone, citral or carvone gauche released from the compounds of formula (I) as prepared in Example 1 and from prior art 3-(dodecylthio)-1-(2,6,6-trimethyl-3-cyclohexen-1-yl)-1-butanone (described as Example 4a in WO 03/049666 in a fabric softener application after drying for 1 day and sampling for 150 min

| Compound tested | delta-damascone released[1] | Factor of increase[2] |
|---|---|---|
| Prior art WO 03/049666 (C12)* | 24.2 | 1.0 |
| (I-isoC3) | 40.9 | 1.7 |
| (I-C4) | 37.8 | 1.6 |
| (I-C5) | 58.2 | 2.4 |

| Compound tested | citral released[1] | Factor of increase[3] |
|---|---|---|
| (II-C4) | 8.8 | 8.8 |
| (II-C5) | 6.4 | 6.4 |
| (II-C6) | 3.6 | 3.6 |

TABLE 1-continued

Average headspace concentrations of delta-damascone, citral or carvone gauche released from the compounds of formula (I) as prepared in Example 1 and from prior art 3-(dodecylthio)-1-(2,6,6-trimethyl-3-cyclohexen-1-yl)-1-butanone (described as Example 4a in WO 03/049666) in a fabric softener application after drying for 1 day and sampling for 150 min

| Compound tested | carvone gauche released[1] | Factor of increase[3] |
|---|---|---|
| (III-C4) | 80.8 | 18.4 |
| (III-C5) | 72.5 | 16.5 |

*= 3-(dodecylthio)-1-(2,6,6-trimethyl-3-cyclohexen-1-yl)-1-butanone
[1]= Amount released [ng/l]
[2]= Factor of increase with respect to the (C12) prior-art reference
[3]= Factor of increase with respect to the corresponding unmodified reference fragrance The data show that the compounds of formula (I) as prepared in Example 1 release more delta-damascone in a fabric softener application after 1 day than the prior art 3-(dodecylthio)-1-(2,6,6-trimethyl-3-cyclohexen-1-yl)-1-butanone (described as Example 4a in WO 03/049666). The compounds of formula (I) as prepared in Example 1 also release more citral or carvone in a fabric softener application after 1 day than the corresponding unmodified free reference fragrance.

The release of delta-damascone from the compounds of formula (I) as prepared in Example 1 was also evaluated olfactively by a panel. For the panel evaluation, the fabric softening surfactant emulsion containing the compound of formula (I) (2.60 g) was prepared as described above. After diluting with demineralised cold tap water (600 g), two cotton sheets were added to each beaker. The sheets were manually stirred for 3 minutes left standing for 2 minutes then wrung out by hand and line-dried. The first sheet was evaluated after drying for 1 day, the second sheet after drying for 3 days. A total of 11 or 12 panelists evaluated the pleasantness of the odor on a scale ranging from −3 to +3, corresponding to an unbearable (−3), acceptable (0) or marvelous (+3) odor.

The results are listed in the Table 2 below.

TABLE 2

Olfactive panel evaluation of the average pleasantness (−3 = unbearable, 0 = acceptable, 3 = marvellous) for the release of delta-damascone from the compounds of formula (I) as prepared in Example 1 in a fabric softener application after drying for 1 day and 3 days

| Compound tested | Pleasantness after drying for 1 day | Pleasantness after drying for 3 days |
|---|---|---|
| (I-C4) | 0.3 | 0.8 |
| (I-C5) | 0.2 | 1.0 |
| (I-C6) | 0.5 | 0.0 |

In the present context one would have expected the odor to be strongly and negatively impacted by the release of the thiol (which is concomitant with the release of the damascene). Thiols have a very strong unpleasant odor perceivable even when only ppm are present. Therefore, any assessment on the pleasantness of the odor in the range from 0 to 3 is an excellent result and unforeseeable from the prior art teaching.

As we can notice from Table 2, after drying for 1 and 3 days, the cotton sheets had an acceptable to pleasant smell, and no badly smelling sulfur odor, reminiscent of volatile alkyl thiols, was detected.

Example 3

Performance of an all Purpose Cleaner Comprising an Invention's Compound of Formula (I) and Comparison with the Prior-Art The use as perfuming ingredient of the present invention's compounds of formula (I) was tested in an all purpose surface cleaner (APC). An APC base with the following final composition was prepared:

| | |
|---|---|
| Neodol ® 91-8 (origin: Shell Chemicals) | 5.0% by weight |
| Marlon ® A 375 (origin: Hüls AG) | 4.0% by weight |
| Sodium cumolsulphonate | 2.0% by weight |
| Kathon ® CG (origin: Rohm and Haas) | 0.2% by weight |
| Water | 88.8% by weight |

The different compounds prepared in Example 1 were weighed into the APC base (1 ml) at a concentration to release a total amount of 0.012 mmol of the fragrance. Then the sample was diluted with demineralized tap water (9 ml). As a reference sample, the prior art compound 3-(dodecylthio)-1-(2,6,6-trimethyl-3-cyclohexen-1-yl)-1-butanone (described as Example 4a in WO 03/049666) or an equimolar amount of the corresponding unmodified free reference fragrance were prepared and treated in the same way. The samples were shaken and then deposited as a film onto a porous ceramic plate (ca. 5×10 cm) by carefully pipetting 0.75 ml of the diluted samples onto the surface of the substrate. The samples were then covered with a ca. 2.5 l crystallizing dish and left standing at room temperature. After one day, the substrates were placed inside a headspace sampling cell (ca. 625 ml) and exposed to a constant air flow of ca. 200 ml/min. The air was filtered through active charcoal and aspirated through a saturated solution of NaCl (to ensure a constant humidity of the air of ca. 75%). During 135 min the headspace system was left equilibrating, and then the volatiles were adsorbed during 15 minutes on a clean Tenax® cartridge. The cartridges were desorbed and analyzed as described in Example 2. All measurements were performed at least twice.

The headspace concentrations measured after 150 min of sampling above the porous ceramic plate are listed in the Table 3 below and compared to the headspace concentrations measured for the release of the fragrance from the prior art compound 3-(dodecylthio)-1-(2,6,6-trimethyl-3-cyclohexen-1-yl)-1-butanone (described as Example 4a in WO 03/049666) or to the corresponding unmodified reference fragrance used as the reference.

TABLE 3

Average headspace concentrations of delta-damascone or carvone gauche released from the compounds of formula (I) as prepared in Example 1 and from prior art 3-(dodecylthio)-1-(2,6,6-trimethyl-3-cyclohexen-1-yl)-1-butanone (described as Example 4a in WO 03/049666) in an all purpose cleaner application after 1 day and sampling for 150 min

| Compound tested | delta-damascone released[1] | Factor of increase[2] |
|---|---|---|
| Prior art WO 03/049666 (C12)* | 16.0 | 1.0 |
| (I-C4) | 51.5 | 3.2 |
| (I-C5) | 59.1 | 3.7 |

TABLE 3-continued

Average headspace concentrations of delta-damascone or carvone gauche released from the compounds of formula (I) as prepared in Example 1 and from prior art 3-(dodecylthio)-1-(2,6,6-trimethyl-3-cyclohexen-1-yl)-1-butanone (described as Example 4a in WO 03/049666) in an all purpose cleaner application after 1 day and sampling for 150 min

| Compound tested | carvone gauche released[1] | Factor of increase[3] |
|---|---|---|
| (III-C4) | 24.7 | 4.7 |
| (III-C5) | 16.5 | 3.1 |
| (III-C6) | 19.9 | 3.8 |

*= 3-(dodecylthio)-1-(2,6,6-trimethyl-3-cyclohexen-1-yl)-1-butanone
[1]= Amount released [ng/l]
[2]= Factor of increase with respect to the (C12) prior-art reference
[3]= Factor of increase with respect to the corresponding unmodified reference fragrance The data show that the compounds of formula (I) as prepared in Example 1 release considerably more delta-damascone in a hard surface cleaner application after 1 day than the prior art 3-(dodecylthio)-1-(2,6,6-trimethyl-3-cyclohexen-1-yl)-1-butanone (described as Example 4a in WO 03/049666). The compounds of formula (I) as prepared in Example 1 also release more carvone gauche in a hard surface cleaner application after 1 day than the corresponding unmodified free reference fragrance.

What is claimed is:
1. A compound of formula

wherein P represents a group susceptible of generating a perfuming α,β-unsaturated ketone or aldehyde represented by one of formulae (P-1) to (P-12), or of any one of its isomers:

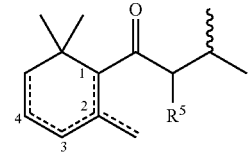

(P-1)

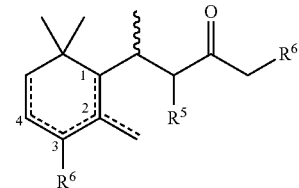

(P-2)

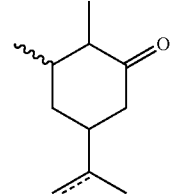

(P-3)

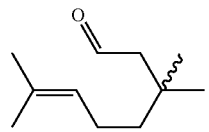

(P-4)

-continued

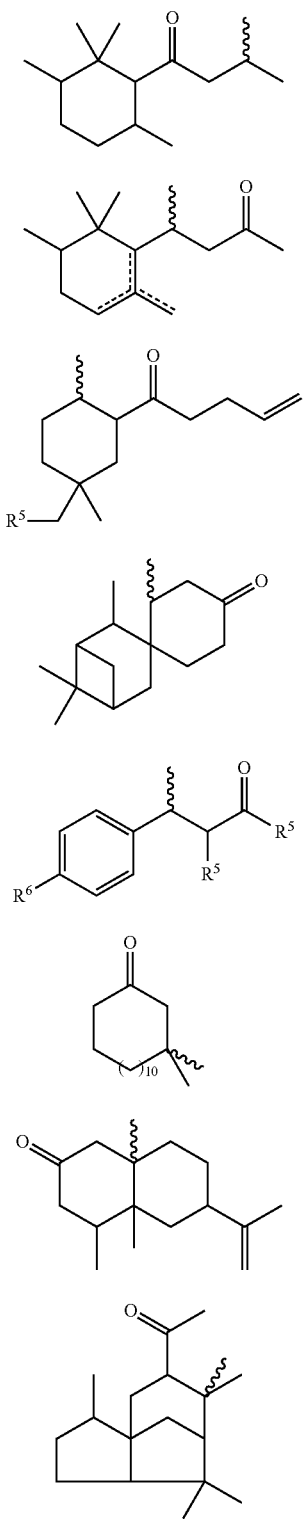

in which the wavy lines indicates the location of the bond between said P and the sulfur atom and the dotted lines represent a single or double bond, R⁵ being a hydrogen atom or a methyl group, and R⁶ representing a hydrogen atom, a hydroxy or methoxy group or a $C_1$-$C_4$ linear or branched alkyl group;

X represents a functional group selected from the group consisting of the formulae i) to iii)

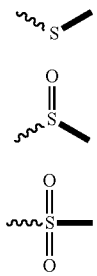

in which formulae the wavy lines are as defined previously and the bold lines indicate the location of the bond between said X and R; and R represents a $C_{3-5}$ alkyl, cycloalkyl or alkenyl group optionally comprising from 1 or 2 functional groups selected amongst $NO_2$, ether, alcohol and thioether.

2. A compound according to claim 1, wherein X represents a functional group of formula i).

3. A compound according claim 2, wherein R represents a $C_{3-5}$ alkyl or cycloalkyl group optionally comprising one functional group selected amongst the ether and thioether groups.

4. A compound according to claim 2, wherein R represents a branched or cyclic alkyl group.

5. A perfuming consumer product which comprises:
i) as perfuming ingredient, at least one compound of formula (I), as defined in claim 2 and
ii) a perfumery consumer base.

6. A compound according to claim 1, wherein R represents a $C_{3-5}$ alkyl or cycloalkyl group optionally comprising one functional group selected amongst the ether and thioether groups.

7. A compound according to claim 6, wherein R represents a branched or cyclic alkyl group.

8. A perfuming consumer product which comprises:
i) as perfuming ingredient, at least one compound of formula (I), as defined in claim 6 and
ii) a perfumery consumer base.

9. A compound according to claim 1, wherein R represents a branched or cyclic alkyl group.

10. A perfuming consumer product which comprises:
i) as perfuming ingredient, at least one compound of formula (I), as defined in claim 9 and
ii) a perfumery consumer base.

11. A perfuming composition comprising:
i) as perfuming ingredient, at least one compound of formula (I) as defined in claim 1;
ii) at least one ingredient selected from the group consisting of a perfumery carrier and a perfumery base; and
iii) optionally at least one perfumery adjuvant.

12. A perfuming composition according to claim 11; which further comprises:
at least one compound selected amongst the isothiazolones of formula

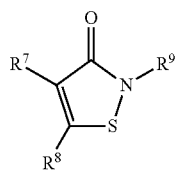 (IV)

wherein $R^7$ and $R^8$ represent, separately and independently of each other, a hydrogen atom, a halogen atom, preferably chlorine, a $C_1$-$C_4$ linear or branched alkyl group, an amino group or a benzylamino group; or, alternatively, $R^7$ and $R^8$ are taken together to represent a phenyl or pyridine ring, possibly substituted with one to four $C_1$-$C_4$ linear or branched alkyl or alkenyl groups and/or one to two halogen atoms, preferably chlorine atoms; and $R^9$ represents a hydrogen atom, an alkali metal atom, in particular Na or K, a phenyl or benzyl group possibly substituted with one or two halogen atoms and/or one or two methyl, trifluoromethyl, methoxy or amino groups, an amine group, or a $C_1$-$C_8$ unsaturated, linear, branched or cyclic hydrocarbon group possibly substituted with one or two nitrogen, oxygen or halogen atoms.

13. A perfuming consumer product which comprises:
   i) a perfuming composition, as defined in claim 12; and
   ii) a perfumery consumer base.
14. A perfuming consumer product which comprises:
   i) a perfuming composition, as defined in claim 11; and
   ii) a perfumery consumer base.
15. A perfuming consumer product which comprises:
   i) as perfuming ingredient, at least one compound of formula (I), as defined in claim 1.
16. A perfuming consumer product according to claim 15, characterized in that the perfumery consumer base is a perfume, a fabric care product, a body-care product, an air care product or a home care product.
17. A perfuming consumer product according to claim 15, characterized in that the perfumery consumer base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.
18. A perfuming consumer product which comprises:
   i) as perfuming ingredient, at least one compound of formula (I), as defined in claim 1 and
   ii) a perfumery consumer base.

* * * * *